(12) United States Patent
Salt et al.

(10) Patent No.: US 11,632,938 B2
(45) Date of Patent: *Apr. 25, 2023

(54) MARKERS FOR DETERMINING THE BIOLOGICAL AGE OF A DOG

(71) Applicant: MARS, INCORPORATED, McLean, VA (US)

(72) Inventors: Carina Salt, Leicestershire (GB); David Allaway, Leicestershire (GB); Phillip Watson, Leicestershire (GB)

(73) Assignee: MARS, INCORPORATED, McLean, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/845,181

(22) Filed: Jun. 21, 2022

(65) Prior Publication Data

US 2022/0361455 A1    Nov. 17, 2022

Related U.S. Application Data

(63) Continuation of application No. 16/971,896, filed as application No. PCT/US2019/018943 on Feb. 21, 2019, now Pat. No. 11,395,478.

(30) Foreign Application Priority Data

Feb. 21, 2018  (GB) ..................................... 1802757

(51) Int. Cl.
*A01K 29/00* (2006.01)
*A61B 5/145* (2006.01)
(Continued)

(52) U.S. Cl.
CPC ........ *A01K 29/005* (2013.01); *A61B 5/14532* (2013.01); *G01N 33/5005* (2013.01);
(Continued)

(58) Field of Classification Search
None
See application file for complete search history.

(56) References Cited

U.S. PATENT DOCUMENTS 8,382,687 B2    2/2013  Lepine et al.
10,264,765 B2   4/2019  Chu
(Continued)

FOREIGN PATENT DOCUMENTS

GB    2 406 642 A       4/2005
WO    WO 03/008973 A2   1/2003

OTHER PUBLICATIONS

U.S. Appl. No. 16/971,896 (2021/0105979), Aug. 21, 2020 (Apr. 15, 2021).
(Continued)

*Primary Examiner* — Thomas S McCormack
(74) *Attorney, Agent, or Firm* — Baker Botts L.L.P.

(57) ABSTRACT

A method for determining the biological age or pace of aging of an adult dog, said method comprising determining the levels of one or more biomarkers selected from the group consisting of (1) blood globulin levels, (2) blood total protein, (3) blood alkaline phosphatase, (4) blood platelet count, (5) blood mean corpuscular volume or (6) urine specific gravity, comparing the results with values obtained from healthy dogs of a known age and of a similar category (toy, small, medium, large or giant). Kits, systems and/or computer media for carrying out the method form further aspects of the invention.

10 Claims, 14 Drawing Sheets

(51) Int. Cl.
  *G01N 33/50* (2006.01)
  *G06K 9/62* (2022.01)
(52) U.S. Cl.
  CPC ......... *G06K 9/6256* (2013.01); *G06K 9/6267* (2013.01); *A61B 2503/40* (2013.01)

(56) References Cited

U.S. PATENT DOCUMENTS

| 2004/0244068 | A1 | 12/2004 | Heaton et al. |
| 2016/0286755 | A1 | 10/2016 | Feng |
| 2020/0072840 | A1 | 3/2020 | Antebi et al. |

OTHER PUBLICATIONS

U.S. Appl. No. 16/971,896, Mar. 22, 2022 Notice of Allowance.
U.S. Appl. No. 16/971,896, Nov. 1, 2021 Response to Non-Final Office Action.
U.S. Appl. No. 16/971,896, Aug. 3, 2021 Non-Final Office Action.
Bae et al., "Models for estimating the biological age of five organs using clinical biomarkers that are commonly measured in clinical practice settings," Maturitas, vol. 75, May 11, 2013, pp. 253-260.
Belsky et al., "Quantification of biological aging in young adults," Proc Natl Acad Sci USA, Jul. 2015, 112(30): E4104-E4110.
International Council for Standardization in Haematology Expert Panel on Cytometry International Society of Laboratory Hematology Task Force on Platelet Counting, Platelet Counting by the RBC/Platelet Ratio Method: A Reference Method, American Journal of Clinical Pathology, vol. 115, Issue 3, Mar. 2001, pp. 460-464.
Karasik et al., "Disentangling the Genetic Determinants of Human Aging: Biological Age as an Alternative the Use of Survival Measures," Journal of Gerontology: Biological Sciences, May 2005, vol. 60A, No. 5, 574-587.
Nakamura et al., "Evaluating measures of hematology and blood chemistry in male rhesus monkeys as biomarkers of aging," Experimental Gerontology, vol. 29, No. 2, pp. 151-177, Mar.-Apr. 1994.
Park et al., "Developing a biological age assessment equation using principal component analysis and clinical 3iomarkers of aging in Korean men," Archives of Gerontology and Geriatrics, vol. 49, No. 1, Jul. 2009, pp. 7-12.
Sebastiani et al., "Biomarker signatures of aging," Aging Cell, vol. 16, No. 2, Jan. 2017, pp. 329-338.

MARKERS FOR DETERMINING THE BIOLOGICAL AGE OF A DOG

CROSS REFERENCE TO RELATED APPLICATIONS

This application is a Continuation of U.S. patent application Ser. No. 16/971,896, filed on Aug. 21, 2020, now allowed, which is a U.S. National Stage Patent Application under 35 U.S.C. § 371 of International Patent Application No. PCT/US2019/018943, filed on Feb. 21, 2019, which claims priority to UK Patent Application Number GB 1802757.3, filed on Feb. 21, 2018, and UK Patent Application Number GB 1809447.4, filed on Jun. 8, 2018, the contents of each of which are hereby incorporated by reference herein in their entirety for any and all purposes, and to each of which priority is claimed.

FIELD

The present invention relates to methods for determining the biological age of a dog, and for determining the pace of aging of a dog, and the system and/or medium for carrying out such methods.

BACKGROUND

As explained by Karasik D. et al., The Journals of Gerontology Series A: Biological Sciences and Medical Sciences, 2005 May 1; 60(5):574-87, biological age estimates the functional status of an individual (based on clinical biochemistry and cell biology measures) in comparison with others of the same chronological age. Different individual rates of aging lead to differences between chronological and biological age, and so individual values of biological age can vary widely at any given chronological age. Ultimately, 'biological age' may serve as an indicator of an individual's general health status and physiological resilience (i.e. the ability to recover from physical or environmental stress), remaining healthy life span, and active life expectancy. Thus, biological age may help in identifying individuals at risk of age-related disorders, serve as a measure of relative fitness, as well as predict disability in later life and mortality independently of chronological age.

Whilst studies of the "pace of aging" has been carried out in humans, in particular to track the efficacy of certain health measures (Belsky et al., Proceedings of the National Academy of Sciences, 2015, Jul. 28:112(30):E4101-10), the applicants are not aware of such studies being reported in companion animals.

In a healthy animal, with a suitable lifestyle in terms of diet, activity levels and access to appropriate veterinary care, the biological age would be expected to be directly related to the chronological age of the animal. However, factors such as poor diets or harsh living conditions may cause a dog to age more quickly. Similarly, a particularly healthy lifestyle involving beneficial diets and exercise levels may lead to a dog having a biological age which is lower than expected as compared to its actual chronological age. The latter is considered to be preferable as this results in an animal which may be healthier overall and have a better longevity.

It would be useful to have a test which provided a clear indication of the biological age of a dog. This will not only provide veterinarians and pet owners with an indication of the general level of health and well-being of dogs but would also allow for assessments to be made to determine the impact of a factor such as particular treatment, diet, exercise level or other lifestyle choice on the health of the dog over time.

There is a need for a clear test which provides reliable and reproducible results in terms of the determination of biological age in dogs.

SUMMARY

The applicants have found that a number of specific biomarkers are particularly useful in determining the biological age of an adult dog, but the size of the dog needs to be taken into account to in order to make an assessment.

According to the present invention there is a provided a method for determining the biological age of an adult dog, said method comprising determining the levels of a biomarker selected from the group consisting of (1) blood globulin levels, (2) blood total protein, (3) blood alkaline phosphatase, (4) blood platelet count, (5) blood mean corpuscular volume or (6) urine specific gravity, comparing the results with values obtained from healthy dogs of a known age and of a similar category (toy, small, medium, large or giant).

As used herein, the expression 'category' refers to the weight category of the particular dog. Categories are defined as follows in Table 1:

TABLE 1

| Size Category name | Weight range of dog |
|---|---|
| Toy | Up to 5 Kg |
| Small | 5-10 Kg |
| Medium | 10-25 Kg |
| Large | 25-40 Kg |
| Giant | Over 40 Kg |

In order to determine which category a particular adult dog falls into, it may be weighed at the time of the test. In particular however, to take account of normal weight variation, the dog is weighed on at least two and preferably at least three separate occasions, for example over a period of from 6-24 months, and the average weight is taken. The dog is then allocated to a particular category on the basis of the mean weight. If the dog is considered to be substantially over or underweight, then this should be taken into account when allocating the dog to a size category. Thus, for example, where a dog is significantly overweight or obese, such that it moves into a higher category as a result of the excess weight, it should be allocated to the category more appropriate to its ideal weight, which will be lower than the actual weight suggests. Conversely, a dog who is significantly underweight may be better allocated to a higher category, more appropriate to its ideal weight.

In a particular embodiment, therefore, the method of the invention involves a preliminary step of determining the weight of an adult dog by weighing the dog, on one or more occasions as described above and allocating the dog to a particular weight category.

Thus the invention may further provide a method for determining the biological age of an adult dog, said method comprising (i) determining the weight of the adult dog, (ii) allocating the dog to a category selected from the group consisting of toy, small, medium, large or giant, (iii) determining the levels of a biomarker selected from the group consisting of (1) blood globulin levels, (2) blood total protein, (3) blood alkaline phosphatase, (4) blood platelet count, (5) blood mean corpuscular volume or (6) urine specific gravity, and (iv) comparing the results with values obtained from healthy dogs of a known age and of a similar category (toy, small, medium, large or giant).

The applicants have surprisingly found that the weight of an adult dog has a significant impact on the specific biomarkers listed above and that each category has a mean age trajectory clearly distinguishable from that of other categories. This makes the estimation of biological age in any particular case clear. Whilst it is widely recognised that the size of a dog can have an impact on longevity, with larger dogs having a relatively shorter lifespan, the applicants are the first to appreciate that the changes are reflected at the biomarker level and that particular biomarkers can be used to allocate a biological age to an adult dog.

As used herein, the expression 'adult dog' refers to a dog who is at least two years old, for example from 2 to 11 years old.

The biomarkers listed above, although previously known in association with specific disease applications, have not been previously directly associated with the determination of biological age. They are generally known to fall within an acceptable range in a healthy dog, but the applicants are generally the first to appreciate that they also vary with time in a manner which is related directly to the size category of the dog.

In particular, blood globulin levels are generally determined with a view to providing a diagnosis of a range of diseases and conditions. In healthy dogs, they would typically be in the range of from 1.8-3.9 g/dL. Low globulin levels for instance, may be an indicator of kidney or liver disease, whereas high levels may indicate the presence of an infection, inflammatory disease or immune disorder, or even some types of cancer.

Blood total protein is measured routinely in combination with the testing for albumin levels to allow the blood globulin level as described above, to be determined. Typically, in healthy dogs, the total protein levels are in the range of from 5.4-7.5 g/dL. High levels of blood total protein in excess of this range can be a sign of dehydration in the dog, for example as a result of failing to drink, or vomiting or chronic diarrhea. Low levels of blood total protein in adult dogs may be indicative of malabsorption syndromes, resulting from food allergies for instance, or intestinal inflammations such as irritable bowel disease.

In a healthy dog, blood alkaline phosphatase (ALK) levels will be in the region of from 24-141 u/L. Increased levels of serum ALK is typically used as a diagnostic marker for liver or heart disease, as well as some genetic disorders of particular breeds. These include Dobermans, Bedlington terriers or West Highland terriers who may be prone to copper storage diseases.

Blood platelet counts are measured to detect thrombocytopenia or thrombocytosis in dogs. Healthy dogs have a blood platelet count between 175,000-200,000 platelets per microlitre of blood. Low values (thrombocytopenia) may be caused by haemorrhaging, for example as a result of trauma or of spontaneous internal bleeding but may also be indicative of underlying disease such as cancers or tick-borne disease. High values (throrabocytosis) may be a temporary response to epinephrine release, but it may be a sign of an underlying bone marrow disease.

Blood mean corpuscular volume (MCV) is typically measured to determine whether a dog is suffering from iron deficiency or liver disease, which may result in a decreased MCV, or regenerative anaemia, which may result in an increase MCV. A typical red blood cell is about 7 microns wide in a healthy dog.

Urine specific gravity, which would normally be about 1.030 in an adult dog, is measured to determine a range of kidney diseases or disorders.

However, the applicants have found that although many biomarkers show a clear and significant change with age, these particular markers showed a clear monotonic response over the adult portion of the lifespan. This means that the response can be easily and reliably translated to provide an accurate measure of biological age.

In particular, in healthy dogs, the levels of blood globulin, total protein, alkaline phosphatase, and platelet count increases with age, whilst the mean corpuscular volume and urine specific gravity reduces with age.

The biomarkers listed above can be determined using conventional methods, and indeed, these are measured as part of many routine blood and urine tests, carried out to determine disease states in an animal. The sample under test is suitably tested using the same analytic method and technique as that used to obtain all the values from the healthy dogs of variable ages.

The methods used typically involve assays that result in spectrophotometric changes (for example, chemical or antibody-linked changes that result in detectable signals at certain wavelengths). These are highly automated and efficient, and form the basis of many normal veterinary health checks. Examples include but are not restricted to, for blood and urine chemistry: IDEXX VetTest; for CBC: scil Vet ABC hematology analyser; also for urine: urine analysis strips.

For instance, total serum protein is often measured using the biuret reaction, in which serum proteins react with copper sulfate in sodium hydroxide to form a violet "biuret" complex. The intensity of the violet color is proportional to the concentration of protein.

Of these proteins, albumin may be measured by binding the albumin to a dye, specifically bromocresol green dye, which forms a stable complex with the albumin. The resultant complex absorbs light at a different wavelength from the unbound dye and so its presence may be detected using a spectrometer. Once this has been determined, the total globulin fraction may be estimated by subtracting the albumin level from the total protein.

Similarly, alkaline phosphatase levels may be determined using a colorimetric enzyme assay, for example, using p-nitrophenyl phosphate (pNPP) as an enzyme substrate as this turns yellow (Amax=405 nm) when dephosphorylated by ALK.

Platelet count may be determined using the International reference method (IRM) as described for example in Am J Clin Pathol 2001; 115:460-464. However, many platelet counters are available commercially, including the Cell-Dyn Sapphire (Abbott Diagnostics, Santa Clara, Calif.), Sysmex XE-2100 (Sysmex, Kobe, Japan), ADVIA 2120 (Siemens Diagnostics, Tarrytown, N.Y.), and Beckman Coulter LH 750 (Beckman Coulter, Miami, Fla.).

Many such automated hematology analyzers can be used to determine mean corpuscular volume also. Alternatively, this can be calculated from hematocrit (Hct) and the red blood cell count (RBC) using a formula such as $$\text{MCV in fl}=(\text{Hct}[\text{in L/L}]/\text{RBC}[\text{in} \times 10^{12}/\text{L}]) \times 1000.$$

Urine specific gravity may also be measured using conventional methods, such as by using a refractometer.

Suitably, more than one of the biomarkers will be determined, in particular, either 2, 3, 4, 5 or all 6 of the biomarkers will be determined in order to provide an accurate assessment of the biological age of a dog. Where multiple biomarkers are tested, the age of the dog can be assessed as the mean of the results obtained. Alternatively, the relationship between the biomarkers may be analyzed and an appropriate algorithm applied to provide the optimum assessment of biological age.

Graphs showing the variant levels with age for the biomarkers used in the method of the invention are illustrated hereinafter, in particular in FIGS. 1-6.

As is clear from these graphs, there is a clear upward or downward trend in the selected biomarkers found within the age range of 2 and 11, and further, that there are quite clear demarcations between the absolute levels and the size of the dog.

Therefore, it would be an easy matter to determine the biological age of a dog by comparing the levels of the particular biomarker with the appropriate one of the graphs, for example the appropriate one of the graphs of FIGS. 1-6, taking account of the size of the dog. Alternatively, the baseline results may be stored, for example, in a computer or computer readable device, and the results from a test subject dog may then be compared with these using an appropriate algorithm, as would be understood in the art. Thus, in a particular embodiment of the method of the invention, the step of comparing the results from a test animal with the known values obtained from healthy animals of known age is carried out in silico.

A computer or a machine-readable cassette programmed to implement such an algorithm may be novel and forms a further aspect of the invention. Computer programming may be carried out by installation of a suitable 'app' for processing data received from a test animal, as described above.

Alternatively, the information may be amenable to formatting as a 'wheel' or slide rule type calculator, so that a biological age may be read by rotating or aligning elements of the calculator to reflect results obtained so that the biological age of a dog of a particular size is indicated and may be read.

In a particular embodiment, where the dog falls into the small or toy category, at least one biomarker other than alkaline phosphatase is evaluated in the method of the invention. This avoids any confusion that may arise as a result of any variability in the response, which has been noted in these dog types, which leads to a graph which is not entirely monotonic in nature.

If required, additional biomarkers may also be included in the method of the invention. These additional biomarkers may be selected from biomarkers measured in the context of routine clinical evaluation of samples, in particular blood samples. Examples of such markers include Glucose (GLU), Amylase (AMYL), Bilirubin, Total (TBIL), Albumin (ALB), Cholesterol (CHOL), Blood Urea Nitrogen (BUN), Creatinine (CREA), Phosphorous (PHOS), Calcium (CA) and alanine aminotransferease or ALT/SGPT (ALT) and Blood Count (CBC): Red Blood Cell Count (RBC), White Blood Cell Count (WBC), Hematocrit (HCT), Hemoglobin (HGB), Mean Corpuscular Hemoglobin (MCH), Mean Corpuscular Hemoglobin Concentration (MCHC), Red Blood Cell Distribution Width (RDW), Mean Platelet Volume (MPV), Granulocyte %, Lymphocyte %, Monocyte % and Eosinophil %. For example, ALB, AMYL, CHOL, Lymphocyte and Monocyte counts may be specifically useful alongside ALKP for more accurate assessment of a specific breed.

Methods for determining these markers are well understood in the art. They include spectrometric analysis, as well as the use of commercially available blood analyzers as discussed above.

Many of these markers have also been found to vary significantly with both age and size of dog as illustrated in FIGS. 7-28 hereinafter. As a result, they may be used to confirm the result obtained using the markers listed above. This may be done by comparing results obtained from a test animal with the appropriate graph herein. Alternatively, the result may be calculated in silico using a computer which has been programmed to carry out this comparison, if necessary with the application of a suitable algorithm.

Following on from this, the method may be used to determine optimal feeding or care regimens for a particular dog. For instance, it is generally understood that while young growing dogs benefit from a high energy/high protein diet, older dogs may have a lower energy requirement, and therefore available diets are modified accordingly. In particular, many manufacturers produce a 'senior' range of dog food which is lower in calories, higher in fiber but has an adequate level of protein and fat for an older dog. Lower protein diets are particularly useful to protect kidney function.

These diets are generally recommended based upon the chronological age of a dog, where these are known. For instance, it may be recommended that a dog is switched onto a 'senior' diet when it is about 7 or 8 years old, or younger, for example 5 years for larger dogs.

However, it is possible that for a particularly healthy animal, this would be inappropriate since the energy levels of the dog could be higher for longer, and a change of diet prematurely may detract from this. Conversely, a prematurely aged dog may benefit from a change of diet at an earlier time, in order to avoid for example, weight gain or obesity which may occur as a result of the feeding of a higher energy food than is necessary. Application of the method of the invention, for example as part of a routine veterinary check, would ensure that decisions regarding change of diet may be taken at a time which is appropriate for the particular dog in question.

The same may be true of other lifestyle choices, such as exercise regimes or fitness programs. In general, activity declines with age but with the use of activity monitors, such as Whistle, it may be possible to track activity against the age of the dog and assess whether advice on exercise regime change is appropriate to the biological age. Use of the invention will allow these options to be tailored to suit a particular dog.

Similarly, where the chronological age of a dog is unknown, for example because it has been a stray or 'rescue' dog, the determination of when to change to a 'senior' diet or to reduce exercise levels may be difficult to decide with any degree of certainty. However, once a biological age has been accorded, on the basis of the present invention, decisions regarding diet and/or lifestyle choices may be optimized for the particular dog.

Thus, in a further aspect, the invention provides a method for selecting a care or dietary regimen for a particular adult dog, said method comprising determining the biological age of the dog using a method described above, and using results obtained to determine a particular care or dietary regimen.

The method of the invention may suitably be carried out more than once, on samples obtained from the same adult dog, over an extended time period, for example, repeatedly once per month or once every 2 years, in particular, from 3 months to 18 months, such as annually during a veterinary health check. The results may then be used to determine the age trajectory or 'pace of aging' of a particular dog. This may be particularly useful in research to test the effects of a particular veterinary treatment, lifestyle choice, such as exercise or diet regimes on the aging process of a dog. Alternatively, it may be used to provide owners with an indication of whether any particular treatment or lifestyle choice impacts on the rate at which their dog is aging.

A high pace of aging in a particular animal may also provide an indication of the risk of the premature development of age-related disorders or conditions. Such conditions may include arthritis, dental diseases, endocrine disorders such as hyperadrenociticism or hypothyroidism, heart disease such as chronic valvular heart disease, diabetes, liver disease, kidney disease, prostate problems, cancer and behavioral or cognitive disorders. In some cases, prophylactic therapies can be administered to a dog identified as being at risk of such disorders due to having an advanced biological age or a particularly fast pace of aging as determined using the method of the invention. Alternatively, monitoring programs can be designed for 'at risk' dogs to check for conditions such as endocrine disorders etc., so that any such conditions can be diagnosed early and treated accordingly.

The method of the invention may be carried out alone or it may be used to corroborate or confirm results of determination of biological age or pace of aging carried out using other methods, which may be biological or physiological in nature.

The method of the invention may be particularly useful in determining the efficacy of a particular dietary or care regimen on the pace of aging of any particular dog. In this case, where a particular dietary or care regimen is selected or prescribed for a dog, assessment of the effect of the dietary or care regimen on the pace of aging of the dog may be determined by carrying out the method of the invention repeatedly using samples from the dog over a period of time, for example at intervals, suitably regular intervals of for example 1-18 months, including before and after the particular dietary or care regimen is introduced. By comparing the pace of aging of the dog before and after change of dietary or care regimen, it will become apparent what effect the change has had on the pace of aging of the dog.

This will be useful for example to the manufacturers of dog foods as it will allow the manufacturer to ensure that new products are developed which help to minimize the pace of aging in dogs of all sizes. Alternatively, it will allow owners or veterinarians to assess the impact of any changes in dietary or care regimens on a particular animal, and, to instigate further changes or modifications to the dietary or care regimen if necessary to ensure that pace of aging is kept low.

In yet a further embodiment, the invention provides a method for determining the efficacy of a particular dietary or care regimen on the pace of aging of a dog, said method comprising:
  i) carrying out the method of the invention repeatedly using samples from the dog over a period of time, before introduction of the particular dietary or care regimen to determine a first pace of aging of the dog,
  ii) carrying out the method of the invention repeatedly using samples from the dog over a period of time after introduction of the particular dietary or care regimen to determine a second pace of aging of the dog,
  iii) comparing the first pace of aging to the second pace of aging to determine the effect of the particular dietary of care regiment on the pace of aging of the dog.

In this context, care regimens may comprise medical treatments, for example, the administration of drugs or medicaments that promote biological pathways that support healthy aging and/or prevent or treat age-related conditions in dogs determined to be at risk of or susceptible to such conditions, or the design of a particular disease monitoring regime, adapted to detect the onset of a particular age-related condition to which an adult dog may be susceptible early, and thereafter, treating the condition appropriately.

Selection of a dietary regimen or therapy will allow the modification of a dog's diet to a 'senior' diet to take place at a time which is particularly suitable for that particular dog.

However, any specialized dietary regimen may be selected depending upon the results obtained. These may include but are not limited to low phosphorous diets, low protein diets, low sodium diets, potassium supplement diets, polyunsaturated fatty acids (PUFA) supplement diets, antioxidant supplement diet, a vitamin B supplement diet, liquid diets, selenium supplement diets, omega 3-6 ratio diets, or diets supplemented with carnitine, branched chain amino acids or derivatives, nucleotides, nicotinamide precursors such as nicotinamide mononucleotide (NMN) or nicotinamide riboside (NR) or any combination thereof.

The diet will be selected by the veterinarian or nutritionist on the basis of the normal skill in the art.

In summary, using data from the Banfield Veterinary network for ostensibly healthy animals, the applicants have been able to show that there are significant differences in the means of many blood, blood count and urine analytes with age and size of dog, and have identified those which are particularly useful in determining the biological age in a reliable manner.

Kits for carrying out the method of the invention may also be provided. In particular, the kits will comprise means for quantitatively determining the levels of one or more of biomarkers (1)-(6) above. Such means may include for example, pieces of kit such as refractometers, to measure urine specific gravity, and/or other devices such as lateral flow devices (a "dip stick" type test) and optical readers to allow for quantitative determination of specific analytes. In a particular embodiment, the kit will comprise an automated analyzer for detecting a particular combination of biomarkers detected in the method of invention.

Kits may also include means to detect one or more of the additional biomarkers listed above.

However, in particular, the method of the invention will be carried out in the context of a veterinary examination, where the specific biomarkers are determined in a laboratory, using the methods outlined above.

Furthermore, as discussed above, algorithms useful in carrying out the methods of the invention may be incorporated into a system specifically adapted to carry out these methods.

Thus, the invention further provides a system for determining the biological age of an adult dog, said system comprising:
  a processor; and
  a memory that stores code of an algorithm that, when executed by the processor, causes the computer system to:
    receive at least one input level of one or more biomarkers relating to the animal, wherein at least one of the one or more biomarkers comprises information relating to (1) blood globulin levels, (2) blood total protein, (3) blood alkaline phosphatase, (4) blood platelet count, (5) blood mean corpuscular volume or (6) urine specific gravity, or any combination thereof;
    receive a second input level relating to a size category of the animal, wherein the size categories are selected from toy, small, medium, large or giant;

analyze and transform the at least one input level of the one or more biomarkers and the second input level to derive a biological age via a classification algorithm, wherein the classification algorithm comprises code developed from a training dataset, the training dataset comprising information relating to said one or more biomarkers from a set of sample animals in each of the size categories;

generate an output, wherein the output is the biological age of the dog;

optionally provide a customized recommendation based on the output for ongoing care or dietary regimen of the dog based upon the biological age; and display the biological age and/or customized recommendation on a graphical user interface.

The sample animals used to define the training dataset for use in the system comprises data obtained from healthy animals of known chronological age in each of the size categories. Suitably, there will be at least 50, for example at least 500, 2000 or 5000 animals of each size category in each set of sample animals. The classification code is then developed by comparing the results from a test animal with the training dataset obtained for healthy animals in the same size category as the test animal. Where more than one biomarker is measured, the biological age determination is made on the basis of each individual biomarker, and the mean of the results are assessed as described above to provide the final classification code.

Furthermore, the invention provides a system for determining the pace of aging of an adult dog comprising:

a processor; and a memory that stores code of an algorithm that, when executed by the processor, causes the computer system to:

receive at least one input level of one or more biomarkers relating to the animal, wherein at least one of the one or more biomarkers comprises information relating to (1) blood globulin levels, (2) blood total protein, (3) blood alkaline phosphatase, (4) blood platelet count, (5) blood mean corpuscular volume or (6) urine specific gravity, or any combination thereof;

receive a second input level relating to a size category of the animal, wherein the size categories are selected from toy, small, medium, large or giant;

analyze and transform the at least one input level of the one or more biomarkers and the second input level to derive a biological age via a prediction algorithm, wherein the prediction algorithm comprises code developed from a training dataset, the training dataset comprising information relating to said one or more biomarkers from a set of sample animals in each of the size categories;

generate a first output, wherein the first output is the biological age of the dog;

compare the first output with at least one third input level comprising the biological age of the said dog determined by the system at, at least, one earlier time point, and a fourth input level which comprises the period of time between the earlier time point and the time at which the biomarkers were obtained from the dog, analyze and transform the first output and the third and fourth input levels so as to determine the pace of aging of the dog;

provide a second output showing the pace of aging of the dog. The system may also provide a customized recommendation for the ongoing care or dietary regimen of the dog, based upon the pace of aging determined, and this customized recommendation is suitably displayed on a graphical user interface.

In particular, such systems may be adapted to determine the effect of a particular dietary or care regimen on the pace of aging of a dog. In such cases, the processor in the system will further generate a fifth input level, which is the pace of aging of the dog determined at a different time point, before or after the dog has been subjected to the particular dietary or care regimen, and analyze and transform the second output and the fifth input level so as to generate a third output indicative of the change of pace of aging. In this case, it may further provide a customized recommendation relating to the modification of the particular dietary or care regiment, with a view to modifying the effects on the pace of aging. The third output and/or the customized recommendation may be displayed on a graphical user interface.

Non-transitory computer-readable mediums storing instructions that, when executed by a processor, cause a computer system to identify biological age of an adult dog, or the pace of aging of a dog, or the effect of a particular dietary or care regimen of a dog and displace results on a graphical user interface in accordance with the systems described above form further aspects of the invention.

If required, the training dataset used in the systems and methods described above may be filtered by a set of inclusion and/or exclusion criteria. Certainly unhealthy animals, or animals who show signs or go on to develop age-related conditions may be excluded from the dataset if required.

DETAILED DESCRIPTION

The invention will now be particularly described by way of example, with reference to the accompanying diagrammatic drawings in which.

EXAMPLE 1

Determination of Key Age-Related Biomarkers

Figure 1:
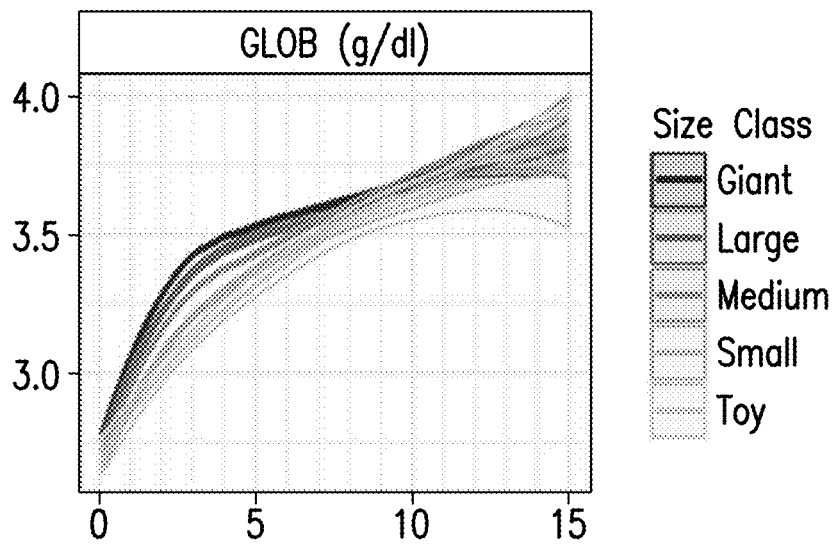
FIG. 1 shows the results for globulin levels in g/dl, on a log scale (y axis) vs age in years (x axis) for dogs of different size categories.

The applicants undertook a major statistical analysis of biomarker data obtained from healthy dogs from a major network of primary care veterinary hospitals (Banfield Veterinary Hospitals). Test results from a 'standard panel' only were included. Other discretionary tests (i.e. the tests outside of the standard panel) are generally from animals potentially suffering from health conditions that would be expected to affect the particular analytes, and so were excluded on the basis that they would provide a less reliable source of trend information.

Also excluded were any tests that were non-numeric, or that were binary/essentially binary (i.e. only a single result value would be considered a 'normal' result), as these were not considered useful for the aim of discovering trends in an essentially healthy population.

After the exclusions mentioned above (i.e. non-standard panel tests and non-numeric and binary tests), the following list of analytes remained in the study.

Blood Chemistry—Alkaline Phosphatase (ALKP), Glucose (GLU), Amylase (AMYL), Bilirubin, Total (TBIL), Protein, Total (TP), Albumin (ALB), Cholesterol (CHOL), Blood Urea Nitrogen (BUN), Creatinine (CREA), Phosphorous (PHOS), Calcium (CA), Globulin (GLOB) and ALT/SGPT (ALT).

Blood Count (CBC)—Red Blood Cell Count (RBC), White Blood Cell Count (WBC), Mean Corpuscular Volume (MCV), Hematocrit (HCT), Hemoglobin (HGB), Mean Corpuscular Hemoglobin (MCH), Mean Corpuscular Hemoglobin Concentration (MCHC), Red Blood Cell.

Distribution Width (RDW), Platelet Count (PLT), Mean Platelet Volume (MPV), Granulocyte %, Lymphocyte %, Monocyte % and Eosinophil %.

Urine—Urine Specific Gravity

Data Extraction

For all the test types (i.e. Blood Chemistry, CBC and Urine), the basic study population was all dogs seen in the above mentioned major network of primary care veterinary hospitals where in-hospital blood/urine diagnostics were performed and:

The animal was not aged over 15 years old at the time of the visit.

The appointment type was not 'emergency/urgent' or 'illness'.

The visit reason was not 'lab result retest', 'poisoning', 'DOA', 'euthanasia' or 'illness recheck'.

There were no 'sick'-flagged diagnoses (except obesity or overweight) given on the visit.

The dog was not euthanised or marked as 'passed away' within one day of the visit.

The tests were not completed multiple times on the same day for the same animal (to avoid inclusion of results which may have been obtained from an analyzer with a suspected malfunction).

Dogs were classified by size, using an individual's mean bodyweight, calculated from all visits in the dataset from age 1.5 years onwards, in accordance with the size categorisation set out above in Table 1—i.e. where 'toy' dogs weighed up to 5 Kg, 'small' dogs weighed from 5-10 Kg, 'medium' dogs weighed from 10-15 Kg, 'large' dogs weighed from 25-40 Kg and 'giant' dogs were over 40 Kg in weight.

In order to remove animals with health conditions that could alter their blood/urine results, further restrictions were put in place according to the type of data, as follows:

Blood Chemistry

Dog should not have been diagnosed with kidney disease, hepatopathy, diabetes mellitus, Cushing's disease, hyperadrenocorticism or a non-specific 'metabolic disorder' during their time at the clinic.

Dog should not have been dispensed/inventoried insulin and/or insulin syringes and/or glucose curve testing at any time (indicative of possible diabetes).

Dog should not have been dispensed/inventoried Cushing's disease medication at any time.

Test should have been carried out between 2010 and 2016 (to ensure similar equipment used in hospitals).

CBC

Dog should not have been diagnosed with kidney disease during their time attending the clinic.

Dog should not have been diagnosed with an infectious disease or a blood disorder within 7 days of the test.

Test should not have been performed at a charter hospital or independent hospital (as they were using a different analyzer model during this time period).

Test should have been carried out between 2010 and 2015 (to ensure similar equipment used in hospitals).

Urine

Dog should not have been diagnosed with kidney disease or diabetes mellitus during their time attending the clinic.

Dog should not have been diagnosed with a urinary system ailment within 7 days of the test.

Dog should not have been dispensed/inventoried insulin and/or insulin syringes and/or glucose curve testing at any time (indicative of possible diabetes).

Test should have been carried out between 2010 and 2014 (to ensure similar equipment used for measurement).

Data cleaning was done analyte-by-analyte. In particular:

Any analyte values recorded in different units to the majority of tests for that analyte were either removed from the dataset in the cleaning stage (CBC data) or not extracted in the first instance (Blood Chemistry and Urine data).

Missing values and negative values, which were considered biologically impossible, were removed for all variables; zero values were also removed for the same reason for all variables except Granulocyte %, Lymphocyte %, Monocyte % and Eosinophil %, where zero values are valid.

Any dogs whose breed size could not be calculated (due to there being no recorded adult weights) were removed from the dataset.

After the above initial cleaning steps, data were split into sets by one-year age bands and breed size. For all variables where there were no zero values, the average skewness over all these groups was then calculated before and after applying a log transformation—where the absolute skewness was reduced by the log transform, indicating that the data distribution was potentially now more 'normal', the log transformation was kept for the remainder of the analysis.

Outliers were detected using the methodology described in 'M. P. J. van der Loo, Distribution based outlier detection for univariate data. Discussion paper 10003, Statistics Netherlands, The Hague (2010)', and applied in the extreme values R package. In brief, the central 80% of the data was used to fit a normal distribution to the data, and data outside of where the most extreme 0.5% of values above and below the mean would be expected to lie were marked as outliers and removed. This was done for each one-year age band x size combination separately, to take account of the probability of changing location and scale across time and different sizes.

Analysis

Analysis of the data was carried out with generalised additive modelling (GAM) techniques, using the mgcv and gamm4 packages in R. The advantage of this methodology is that it allows the mean (and in some cases other aspects of the data, such as the standard deviation) to be modelled with a spline function which is not required to have a closed form equation (i.e. it doesn't have to be, say, linear or polynomial), giving the model more 'freedom' to describe the data.

Two different models were run—one which modelled both the mean and (log) standard deviation as smooth functions of time, and one which only modelled the mean but which was able to give estimates of between and within animal variance. The second model was used to estimate how the error variance of the first model is likely to be split up into within and between animals.

Residuals from both models were assessed with normal scores plots, histograms and fitted vs. residual plots.

Further details of the two models are as follows:

Model 1—Model 1 was a type of GAM model called a Gaussian location scale additive model, which modelled both the mean and the log of the standard deviation as smooth functions (thin plate regression splines) of time, differently for each size category (dog). As the Gaussian location scale additive model was not able to incorporate random terms, this model was run on a dataset consisting of a randomly chosen observation from each animal in the dataset.

Model 2—Model 2 was a generalised additive mixed model (GAMM), which modelled the mean as for model 1, but assumed a constant variance. An additive random term was added for each individual. As this model was difficult to converge in a practical timescale when applied to the entire dataset, it was instead built upon a smaller subset consisting of all visits from a 1 in 20 sample of all individuals.

For all models, the smoothing parameter left at the default value, and some further smoothing was applied to the prediction plots to even out some jagged points.

Figure 2:
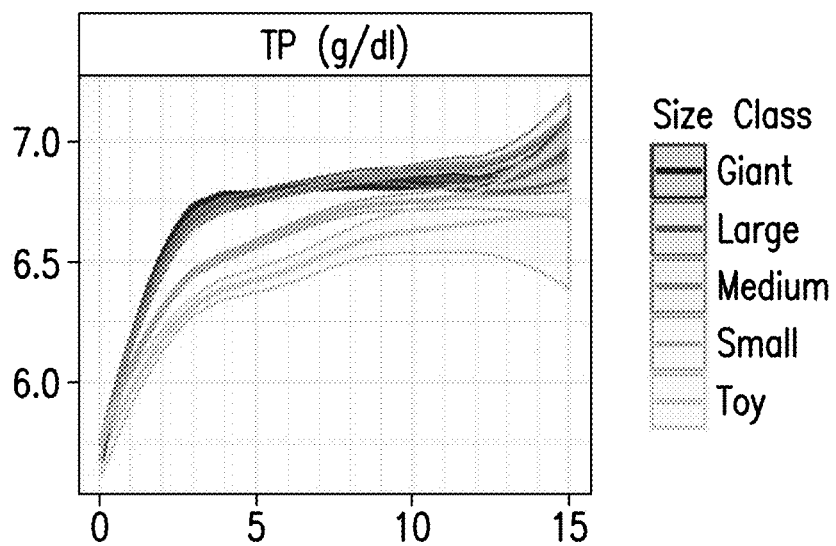
FIG. 2 shows the results for total protein (TP) in g/dl, on a log scale (y axis) vs age in years (x axis) for dogs of different size categories.
Figure 3:
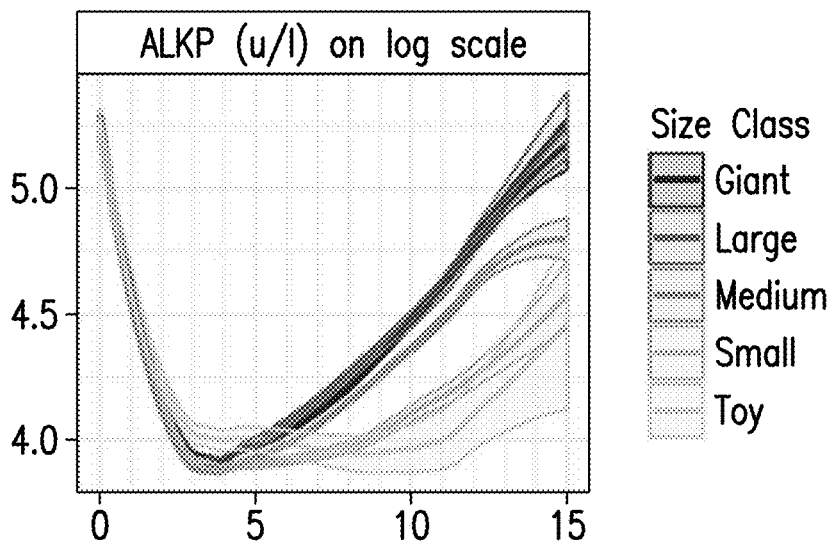
FIG. 3 shows the results for alkaline phosphatase (ALK) levels in International units/litre ($\mu$/L), on a log scale (y axis) vs age in years (x axis) for dogs of different size categories.
Figure 4:
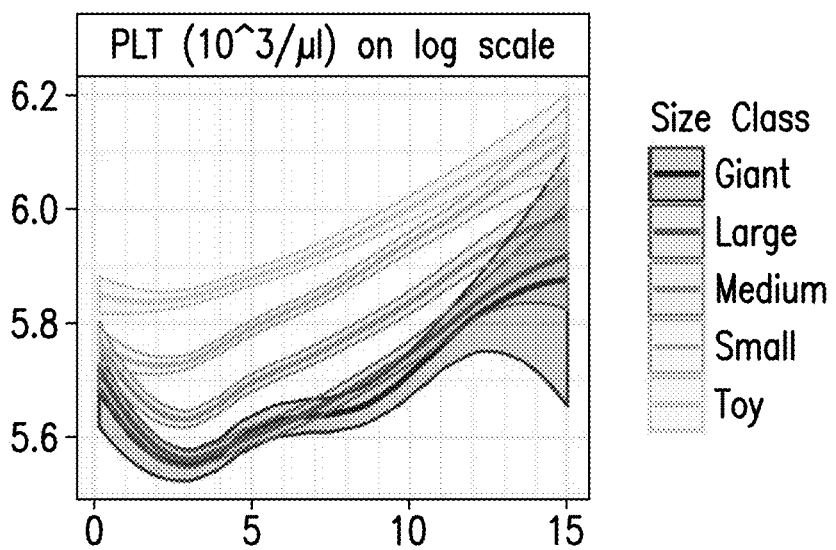
FIG. 4 shows the results for platelet count as $10^3/\mu L$, on a log scale (y axis) vs age in years (x axis) for dogs of different size categories.
Figure 5:
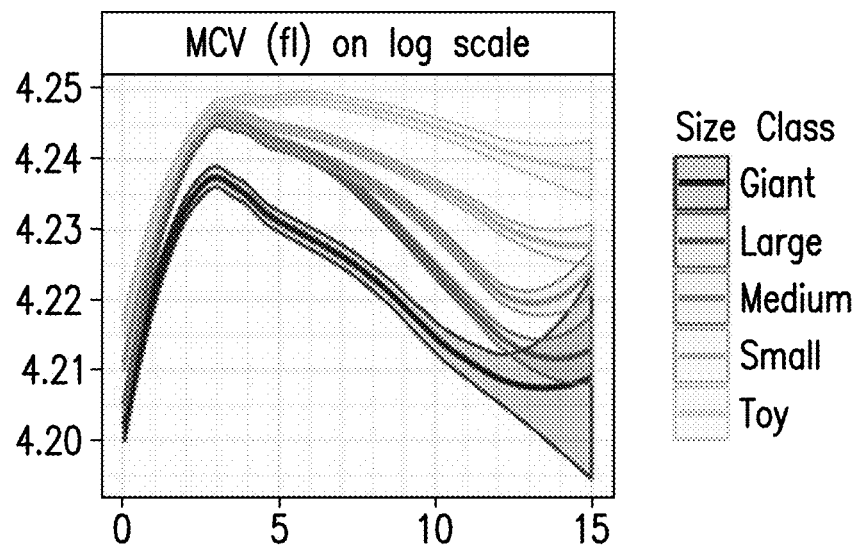
FIG. 5 shows the results for mean corpuscular volume in fl on a log scale (y axis) vs age in years (x axis) for dogs of different size categories.
Figure 6:
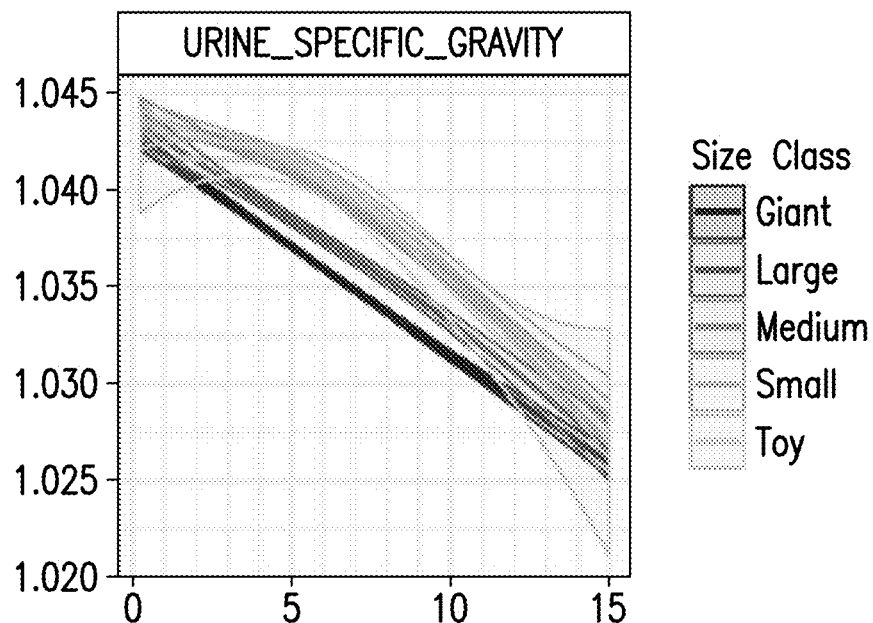
FIG. 6 shows the results for urine specific gravity vs age in years (x axis) for dogs of different size categories.
Figure 7:
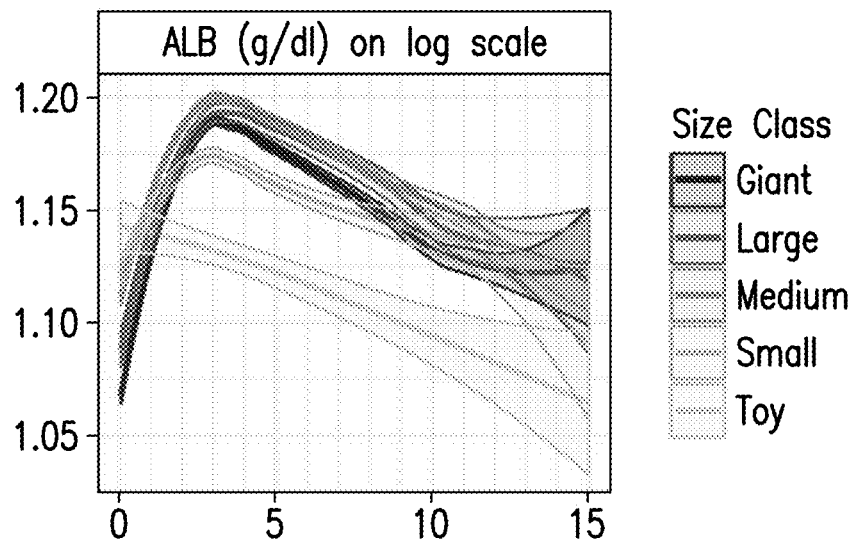
FIG. 7 shows the results for albumin levels in g/dl, on a log scale (y axis) vs age in years (x axis) for dogs of different size categories.
Figure 8:
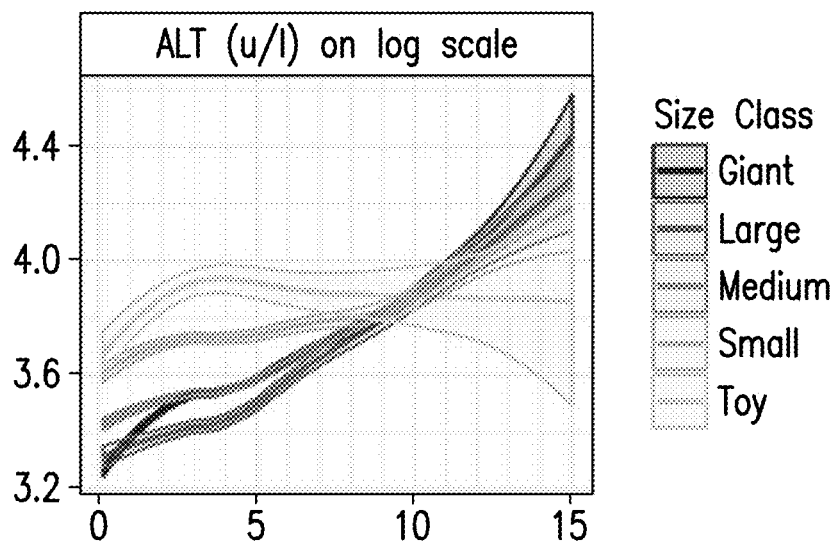
FIG. 8 shows the results for ALT levels in International units/1 (u/l), on a log scale (y axis) vs age in years (x axis) for dogs of different size categories.
Figure 9:
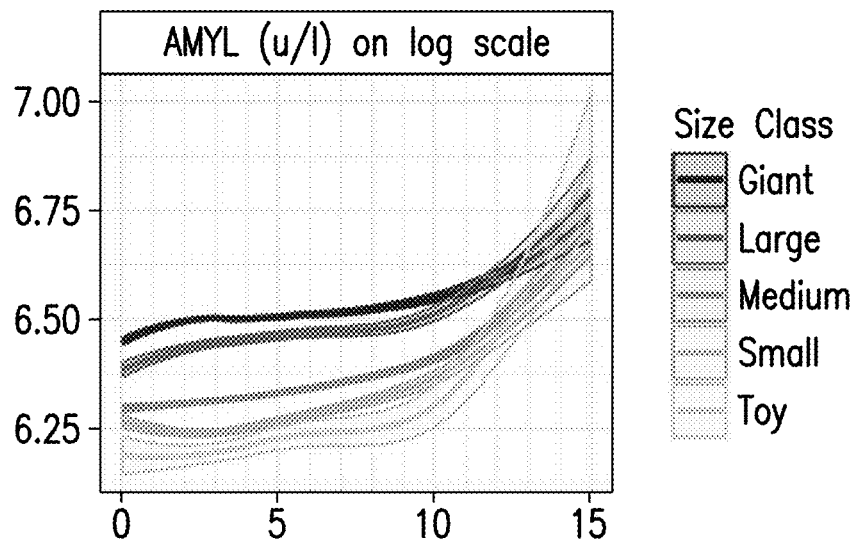
FIG. 9 shows the results for amylast (AMYL) levels in International units/1 (u/l), on a log scale (y axis) vs age in years (x axis) for dogs of different size categories.
Figure 10:
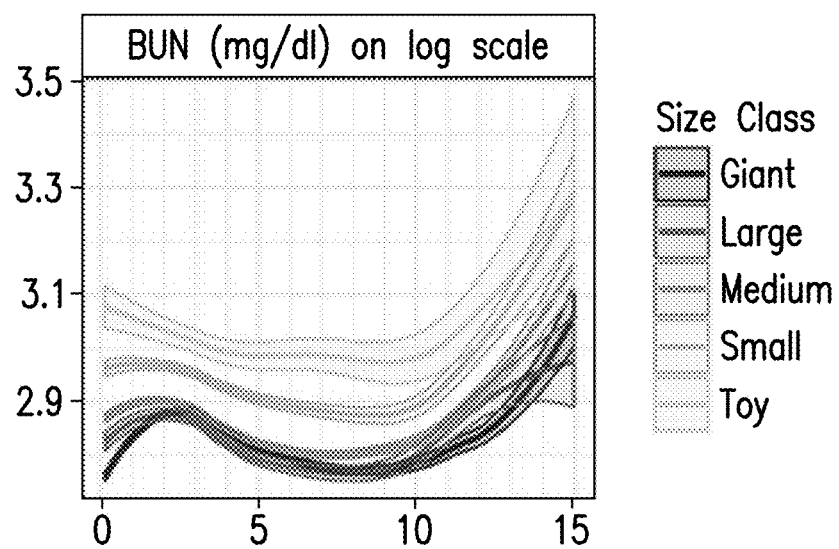
FIG. 10 shows the results for blood urea nitrogen (BUN) levels in mg/dl, on a log scale (y axis) vs age in years (x axis) for dogs of different size categories.
Figure 11:
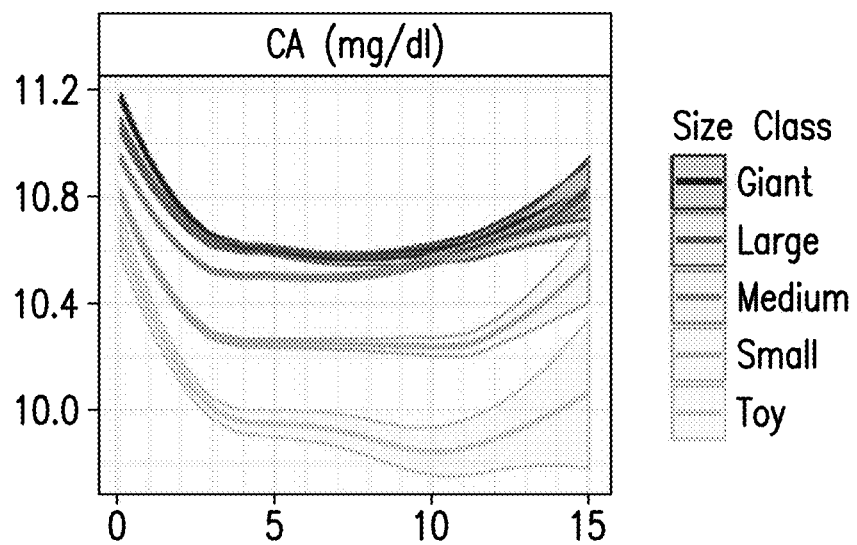
FIG. 11 shows the results for calcium levels in mg/dl, (y axis) vs age in years (x axis) for dogs of different size categories.
Figure 12:
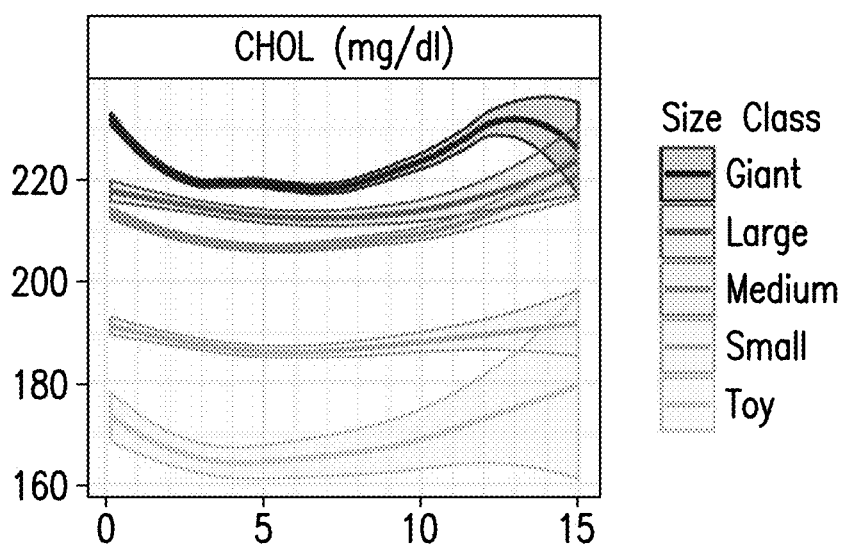
FIG. 12 shows the results for cholesterol (CHOL) levels in mg/dl, (y axis) vs age in years (x axis) for dogs of different size categories.
Figure 13:
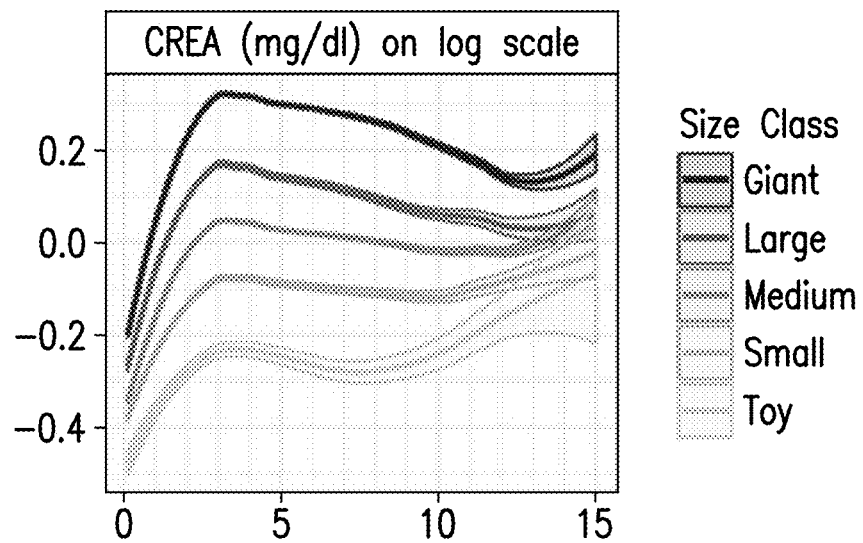
FIG. 13 shows the results for creatine (CREA) levels in mg/dl, on a log scale (y axis) vs age in years (x axis) for dogs of different size categories.
Figure 14:
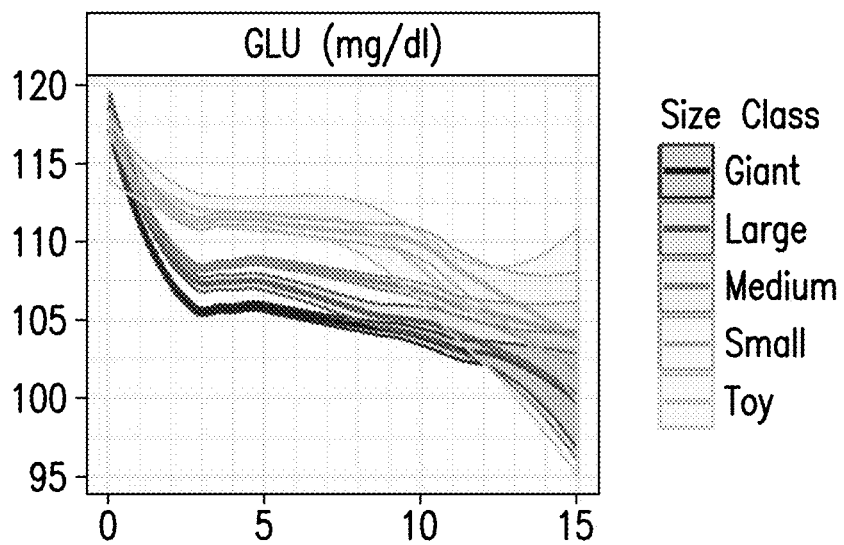
FIG. 14 shows the results for glucose (GLU) levels in mg/dl, (y axis) vs age in years (x axis) for dogs of different size categories.
Figure 15:
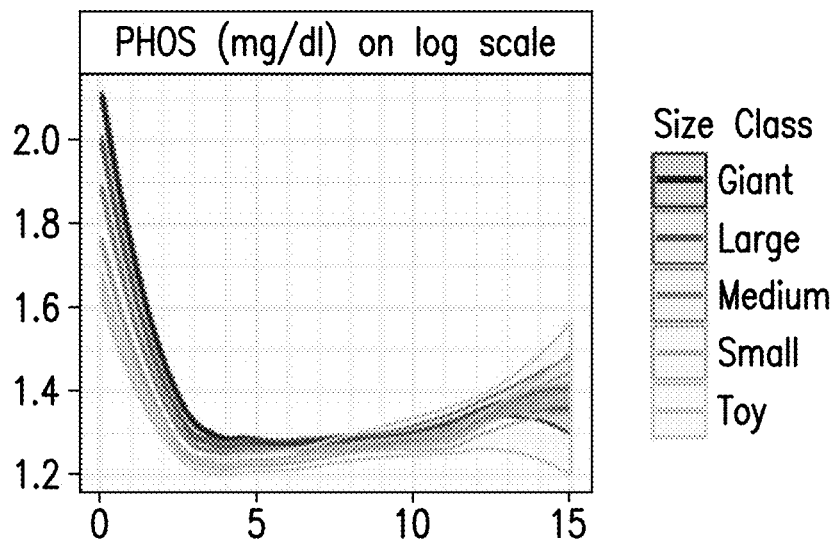
FIG. 15 shows the results for phosphorus (PHOS) levels in mg/dl, on a log scale (y axis) vs age in years (x axis) for dogs of different size categories.
Figure 16:
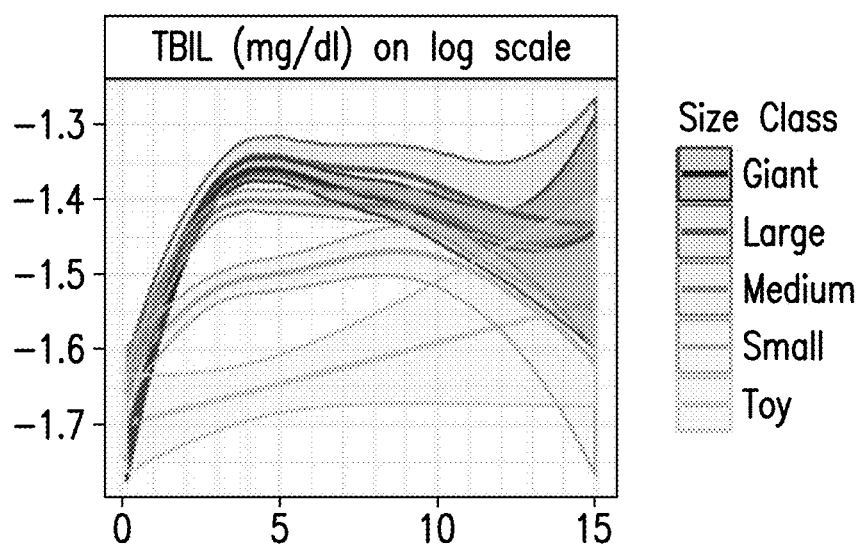
FIG. 16 shows the results for total Bilirubin levels (TBIL) in mg/dl, on a log scale (y axis) vs age in years (x axis) for dogs of different size categories.
Figure 17:
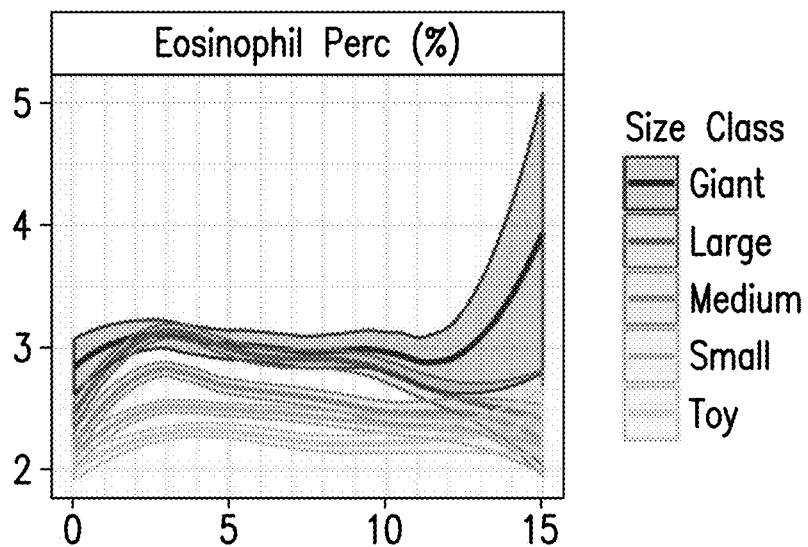
FIG. 17 shows the results for eosinophil percentage (%)(y axis) vs age in years (x axis) for dogs of different size categories.
Figure 18:
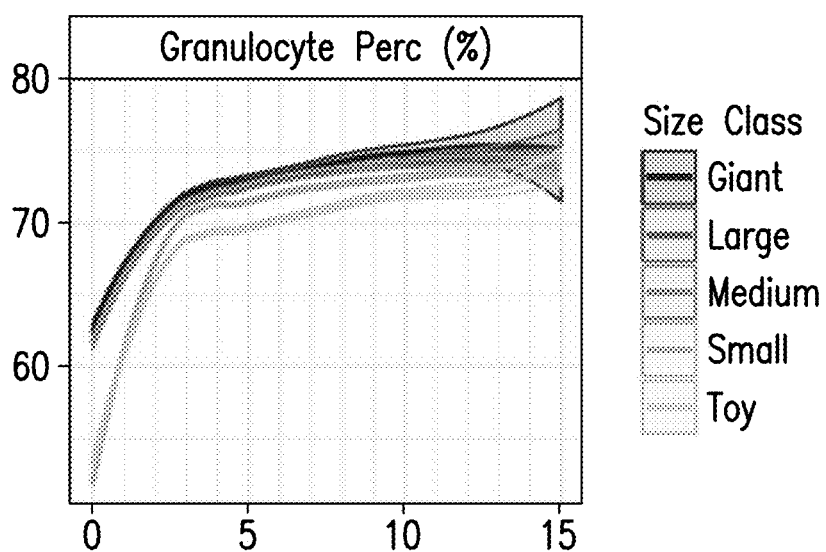
FIG. 18 shows the results for granulocyte percentage (%) (y axis) vs age in years (x axis) for dogs of different size categories.
Figure 19:
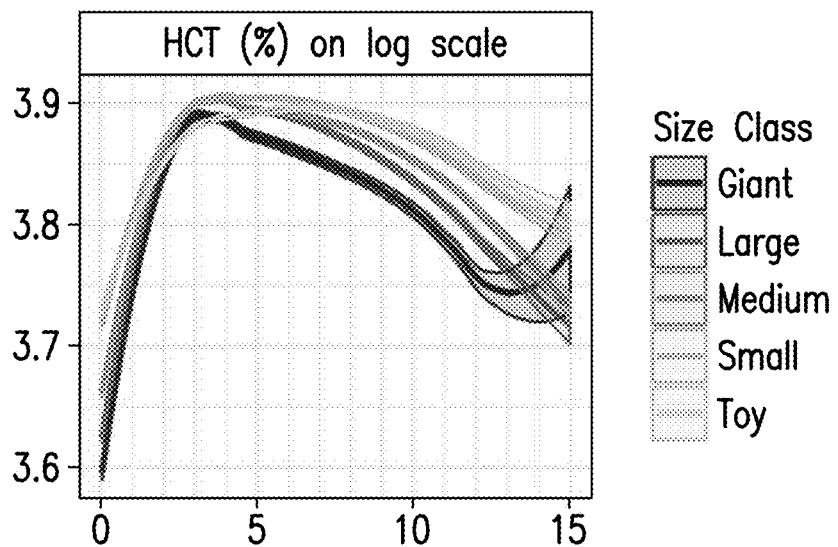
FIG. 19 shows the results for hematocrit (HCT) percentage (%), on a log scale (y axis) vs age in years (x axis) for dogs of different size categories.
Figure 20:
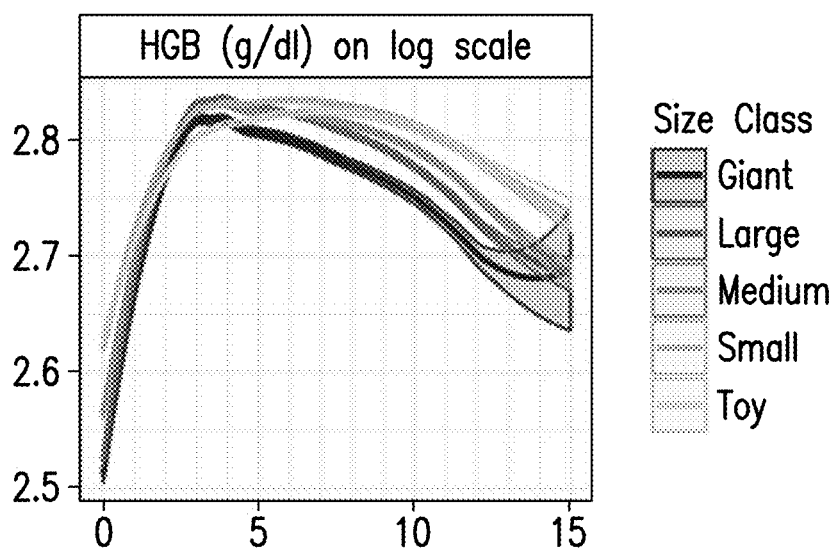
FIG. 20 shows the results for hemaglobin levels (HGB) in g/dl, on a log scale (y axis) vs age in years (x axis) for dogs of different size categories.
Figure 21:
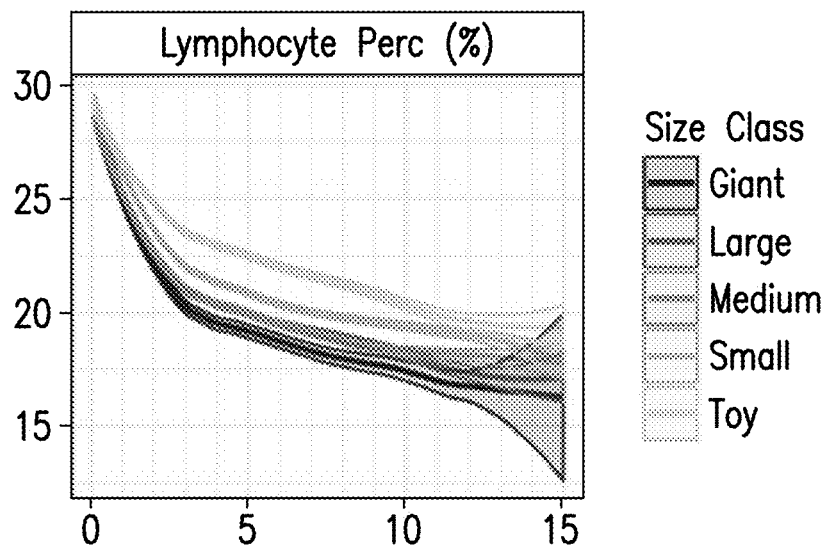
FIG. 21 shows the results for lymphocyte percentage (%) (y axis) vs age in years (x axis) for dogs of different size categories.
Figure 22:
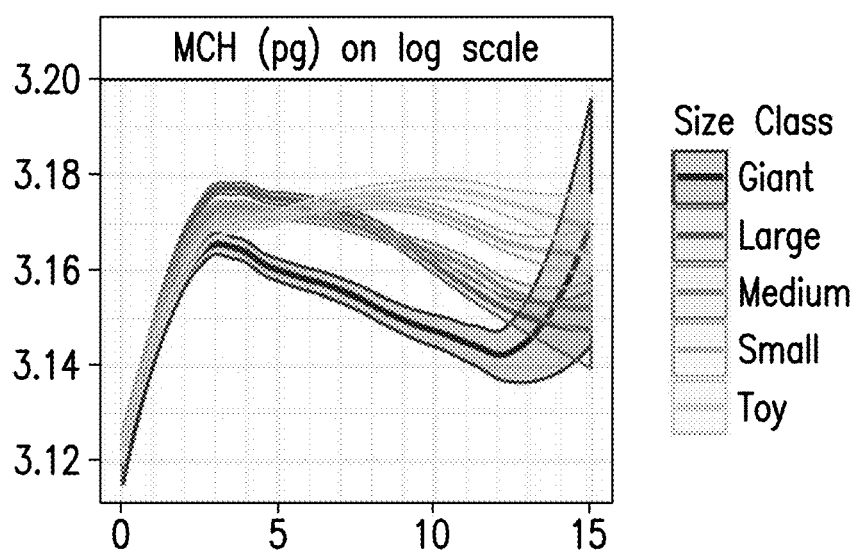
FIG. 22 shows the results for mean corpuscular haemoglobin (MCH) levels (TBIL) in pg, on a log scale (y axis) vs age in years (x axis) for dogs of different size categories.
Figure 23:
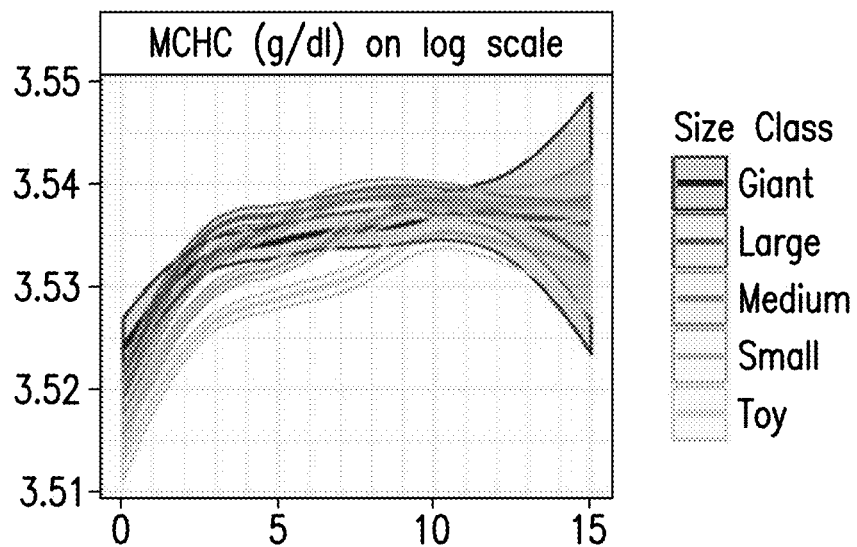
FIG. 23 shows the results for mean corpuscular haemoglobin concentration (MCHC) in mg/dl, on a log scale (y axis) vs age in years (x axis) for dogs of different size categories.
Figure 24:
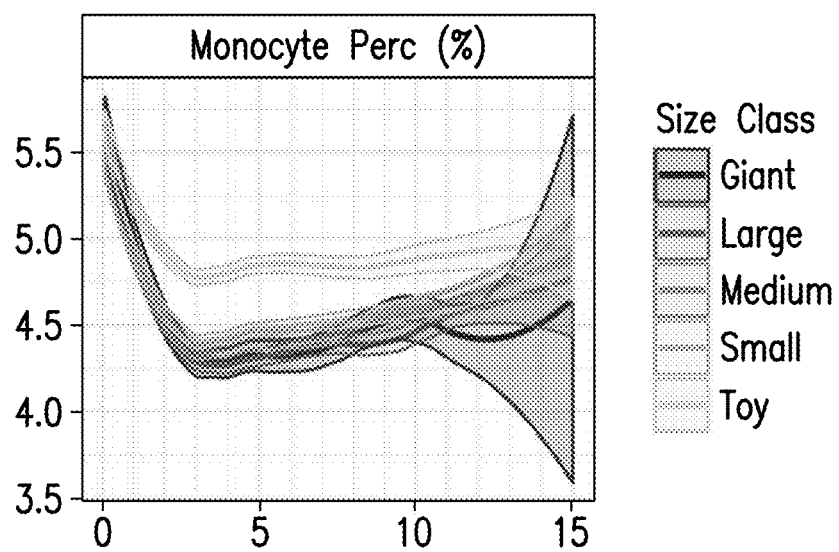
FIG. 24 shows the results for blood monocyte percentage (%) (y axis) vs age in years (x axis) for dogs of different size categories.
Figure 25:
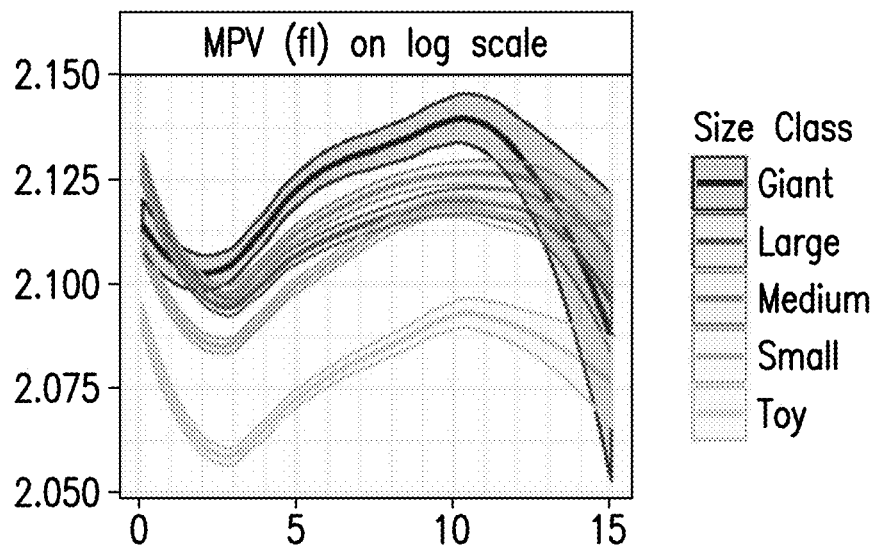
FIG. 25 shows the results for mean platelet volume (MPV) in fl, on a log scale (y axis) vs age in years (x axis) for dogs of different size categories.
Figure 26:
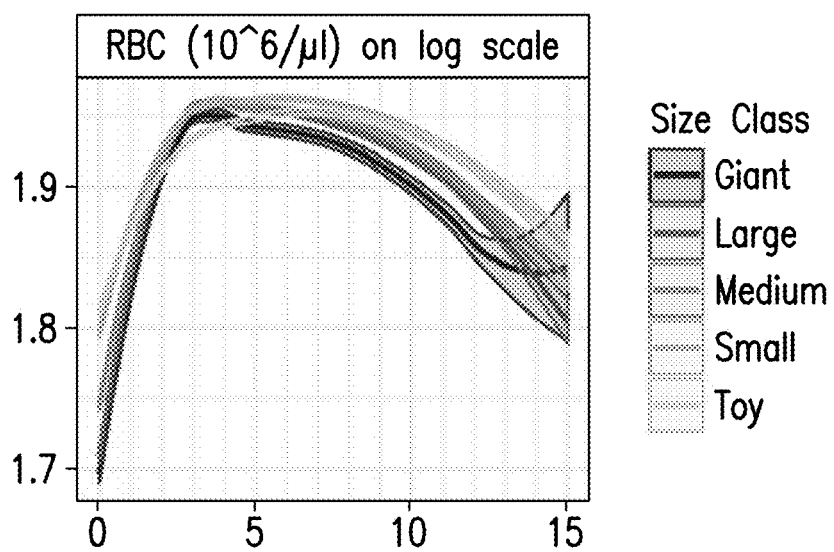
FIG. 26 shows the results for red blood cell count (RBC) in $10^6/\mu l$, on a log scale (y axis) vs age in years (x axis) for dogs of different size categories.
Figure 27:
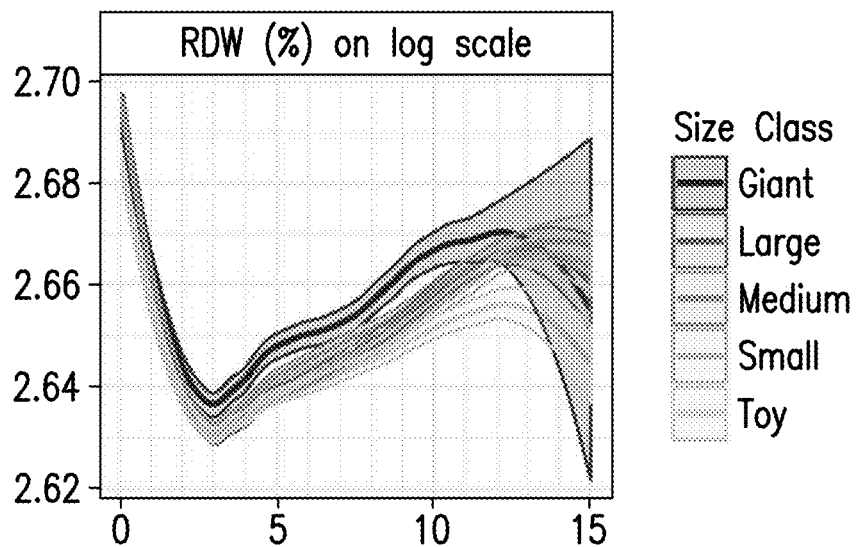
FIG. 27 shows the results for red blood cell distribution width (RDW) in %, on a log scale (y axis) vs age in years (x axis) for dogs of different size categories.
Figure 28:
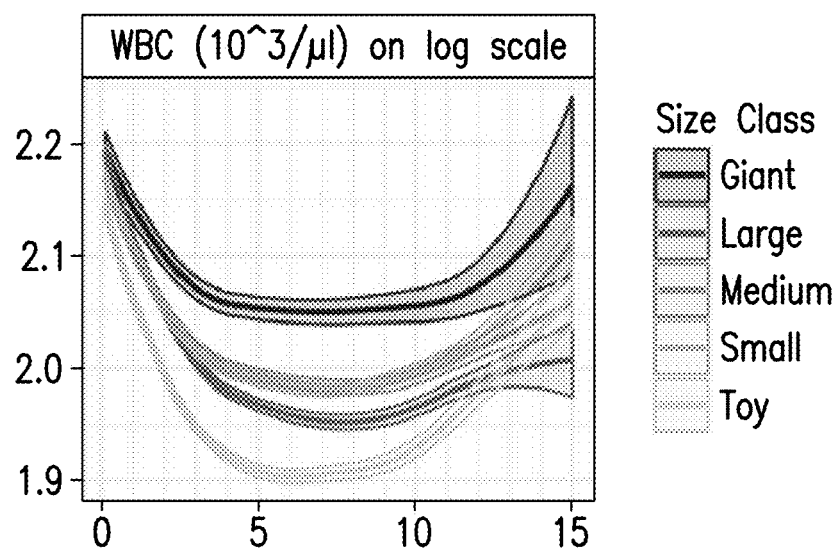
FIG. 28 shows the results for white blood cell count (WBC) in $10^3/\mu l$, on a log scale (y axis) vs age in years (x axis) for dogs of different size categories.

The results from model 1 were illustrated as plots of the predicted mean and predicted standard deviation with age for each analyte, together with a 95% confidence interval for the prediction. These were still on the log scale where a log transformation had been employed. Results are shown in FIGS. 1-28.

Further plots illustrated the predicted value of each analyte by age, together with a 95% prediction interval (i.e. a confidence interval for a single point) on the original scale; results from model 2 were used to approximately divide this interval into between-animal and within-animal intervals (illustrating—respectively—how much the mean for a new animal could vary about the population mean and how much a single point for a new animal could vary about the population mean). It should be noted that the confidence and prediction intervals were unadjusted in this case.

The age interval of special interest (4-8 years) was examined from these graphs, to gain an insight into which analytes tended to have a roughly monotonic (i.e. increasing or decreasing) relationship with age during this range. For these analytes, on the scale of the linear predictor, the difference between the values at 4 and 8 years of age were expressed on the standard deviation scale in order to give some indication of the magnitude of the difference relative to the noise in the data.

Results

Dataset Size

The sizes of the datasets used (after cleaning) are given in the table 2 below:

TABLE 2

|  | Model 1 | Model 2 |
| --- | --- | --- |
| Blood Chemistry | 1.4m | 180k |
| CBC | 1.8m-2.0m (exceptPLT which was 450k) | 276k-344k (exceptPLT which was 41k) |
| Urine | 390k | 110k |

Model Fit

Model 1 (as described above) was successfully fitted to all analytes. With the exception of Granulocyte %, Lymphocyte %, Monocyte % and Eosinophil %, all the models showed well fitted residuals (i.e. close to normally distributed). The results for the four exceptions (some of which included multiple zero values which contributed to the strange residual pattern) should be treated with caution.

Model Results

Graphs showing the predicted means and standard deviations (SDs) (with 95% CIs) from Model 1 for each blood chemistry, CBC and urine analyte were analyzed. These are on the 'scale of the linear predictor' i.e. on a log scale if the analyte was log transformed.

Graphs showing the predicted means on the original scale, with 95% prediction intervals, for large dogs only. These were plotted for only one dog category as an illustration because the graphs became too noisy with all plotted together.

These results showed that, for all the analytes, the means show clear and significant changes with age (for all sizes). This is especially pronounced at the younger life stages, with many showing a distinct change at around 2-3 years of age e.g. PHOS and TP. However, some analytes, such as ALB, PLT and GLOB show a fairly steady change in the mean from around 2-4 years onwards, whilst others show little change in the mid years only to rise or fall sharply in older age, for example BUN.

All the analytes showed an obvious (and significant) effect of size, and this pattern often followed the same logical ordering of the sizes, at least approximately (e.g. CHOL, CREA and MPV) which adds more weight to this being a real effect. The effect of size was not always as clear in the predicted SDs (e.g. BUN and TP have rather similar SD profiles, despite there being a size effect visible in the predicted means) although sometimes it was (e.g. GLU has a predicted SD that increases with decreasing breed size category).

However, the effects of these differences was very often dwarfed by the size of the predicted SD i.e. the level of noise in the data is large compared to the differences in the means that are associated with age or size. This can be seen clearly in the graphs with prediction intervals given (essentially confidence intervals for a new single point). Exceptions were normally around the age related differences seen in early life (e.g. PHOS) rather than differences associated with aging, however.

The split of the noise across between-individual and within-individual (i.e. individual to individual variability vs 'true' noise around the mean for a single individual) varied. In some e.g. CHOL, the majority appeared to be between individual (i.e. this could be a measure that is quite variable across individuals but tends to be quite consistent within one dog) whereas in others, e.g. TBIL, the majority appeared to be within individual (i.e. this could potentially be an analyte that varies a lot day to day within an individual or a test with a high measurement error).

Table 3 summarises where a consistent trend was seen in the age range of interest and expresses the change in each analyte on the SD scale (so the larger this quantity is, the greater the change relative to the noise in the data).

TABLE 3

| Type | Analyte | Monotonic trend | Change between 4-8 years on SD scale |
|---|---|---|---|
| Blood Chemistry | ALB | Y | 0.112 |
| | ALKP | Y(except toy and small) | 0.289 |
| | ALT | Y(except toy and small) | 0.168 |

TABLE 3-continued

| Type | Analyte | Monotonic trend | Change between 4-8 years on SD scale |
|---|---|---|---|
| | AMYL | Y | 0.155 |
| | BUN | Y | 0.094 |
| | CA | N | 0.120 |
| | CHOL | Y | 0.076 |
| | CREA | Y | 0.098 |
| | GLOB | Y | 0.413 |
| | GLU | N | 0.153 |
| | PHOS | Y | 0.128 |
| | TBIL | N | 0.046 |
| | TP | Y | 0.327 |
| CBC | Eosinophil Perc | Y(except toy and small) | 0.030 |
| | Granulocyte Perc | N | 0.275 |
| | HCT | Y | 0.143 |
| | HGB | Y | 0.139 |
| | Lymphocyte Perc | N | 0.283 |
| | MCH | Y | 0.127 |
| | MCHC | N | 0.041 |
| | MCV | Y | 0.242 |
| | Monocyte Perc | Y | 0.012 |
| | MPV | Y | 0.067 |
| | PLT | Y | 0.276 |
| | RBC | Y | 0.072 |
| | RDW | N | 0.212 |
| | WBC | Y | 0.081 |
| Urine | Urine specific gravity | Y | 1.370 |

This table suggests that the analytes which show both a monotonic trend in the age range of interest and have the most favourable (i.e. highest) difference across that age range relative to the noise in the data (i.e., an SD of greater than 0.2) are as follows:

Urine Specific Gravity, GLOB, TP, ALKP (not for toy or small dogs), MCV and PLT, and the results for these biomarkers are shown in FIGS. 1-6.

As a result, these markers and indeed, these graphs, may be used in a determination of biological age, using the method of the invention.

The additional biomarkers may also be utilised to confirm or refine the results since these also show a clear and distinct trajectory depending upon age, albeit not in a monotonic manner.

The invention claimed is:

1. A computer system for determining the biological age of a dog, comprising:
   a. a processor; and
   b. a memory storing algorithm that, when executed by the processor, cause the computer system to:
      i. receive first and second inputs relating to the dog, wherein the first input is selected from the group consisting of blood globulin, blood total protein, blood alkaline phosphatase, blood platelet count, blood mean corpuscular volume, and urine specific gravity, and wherein the second input is a size category of the dog;
      ii. compare the first input of the dog to a reference value stored in a training dataset comprising inputs of the size category of the dog;
      iii. generate, based on the comparing, an output comprising the biological age of the dog;
      iv. display on a graphical user interface a customized recommendation comprising an exercise regimen based on the biological age of the dog.

2. The computer system of claim 1, wherein the training dataset comprises data obtained from healthy animals of known chronological age.

3. The computer system of claim 1, wherein the size category is selected from the group consisting of toy, small, medium, large, and giant.

4. The computer system of claim 1, further comprising receiving a third input relating to the dog and selected from the group consisting of glucose, amylase, total bilirubin, albumin, cholesterol, blood urea nitrogen, creatinine, phosphorous, calcium, ALT/SGPT, blood count, red blood cell count, white blood cell count, hematocrit, hemoglobin, mean corpuscular hemoglobin, mean corpuscular hemoglobin concentration, red blood cell distribution width, mean platelet volume, percentage of granulocytes, percentage of lymphocytes, percentage of monocytes, and percentage of eosinophils.

5. The computer system of claim 1, wherein the system is a non-transitory system.

6. A method for reducing risk of developing an age-related condition in an adult dog, the method comprising:
   a. weighing the dog and assigning a size category;
   b. determining a level of blood globulin, blood total protein, blood alkaline phosphatase, blood platelet count, blood mean corpuscular volume, urine specific gravity, or a combination thereof;
   c. comparing the levels with reference values of healthy dogs of the size category;
   d. determining, based on the comparing, the biological age of the dog;
   e. administering exercise to reduce a risk of developing an age-related condition.

7. The method of claim 6 further comprising obtaining a biological sample from the dog.

8. The method of claim 6, wherein the size category is selected from the group consisting of toy, small, medium, large, and giant.

9. The method of claim 6, wherein c) further comprises determining the level of glucose, amylase, total bilirubin, albumin, cholesterol, blood urea nitrogen, creatinine, phosphorous, calcium, ALT/SGPT, blood count, red blood cell count, white blood cell count, hematocrit, hemoglobin, mean corpuscular hemoglobin, mean corpuscular hemoglobin concentration, red blood cell distribution width, mean platelet volume, percentage of granulocytes, percentage of lymphocytes, percentage of monocytes, percentage of eosinophils, or a combination thereof.

10. The method of claim 1, wherein the age-related condition is selected from the group consisting of arthritis, dental disease, hyperadrenociticism, hypothyroidism, heart disease, chronic valvular heart disease, diabetes, liver disease, kidney disease, behavioral disorders, and cognitive disorders.

* * * * *